(12) United States Patent
Miyata et al.

(10) Patent No.: US 8,852,126 B2
(45) Date of Patent: Oct. 7, 2014

(54) MEDICAL GUIDEWIRE

(75) Inventors: Naohiko Miyata, Nagoya (JP); Satoshi Nagano, Nagoya (JP); Makoto Nishigishi, Nagoya (JP)

(73) Assignee: Asahi Intecc Co., Ltd., Nagoya (JP)

( * ) Notice: Subject to any disclaimer, the term of this patent is extended or adjusted under 35 U.S.C. 154(b) by 813 days.

(21) Appl. No.: 12/813,093

(22) Filed: Jun. 10, 2010

(65) Prior Publication Data

US 2010/0318066 A1 Dec. 16, 2010

(30) Foreign Application Priority Data

Jun. 16, 2009 (JP) ................. 2009-143633

(51) Int. Cl.
 *A61B 5/00* (2006.01)
 *A61M 25/00* (2006.01)
 *A61M 25/09* (2006.01)

(52) U.S. Cl.
 CPC ..... *A61M 25/09* (2013.01); *A61M 2025/09175* (2013.01)
 USPC ........................................ 600/585

(58) Field of Classification Search
 USPC ........................................ 600/585
 See application file for complete search history.

(56) References Cited

U.S. PATENT DOCUMENTS

| | | | |
|---|---|---|---|
| 5,345,945 A | 9/1994 | Hodgson et al. | |
| 7,077,811 B2 * | 7/2006 | Vrba et al. | 600/585 |
| 7,252,643 B2 * | 8/2007 | Fujimoto et al. | 600/585 |
| 7,878,984 B2 * | 2/2011 | Jacobsen et al. | 600/585 |
| 7,883,474 B1 * | 2/2011 | Mirigian et al. | 600/585 |
| 2004/0116833 A1 | 6/2004 | Kato et al. | |
| 2004/0122340 A1 | 6/2004 | Vrba et al. | |
| 2004/0210163 A1 | 10/2004 | Osawa et al. | |
| 2006/0014418 A1 | 1/2006 | Kato et al. | |
| 2006/0235337 A1 | 10/2006 | Vrba et al. | |
| 2007/0083132 A1* | 4/2007 | Sharrow | 600/585 |
| 2008/0214959 A1 | 9/2008 | Miyata et al. | |

FOREIGN PATENT DOCUMENTS

| | | | |
|---|---|---|---|
| CN | 1537645 A | | 10/2004 |
| CN | 101209365 A | | 7/2008 |
| EP | 982046 A1 | * | 3/2000 |
| EP | 0982046 A1 | | 3/2000 |
| JP | 08-173547 A | | 7/1996 |
| JP | 09-182800 | | 7/1997 |

(Continued)

OTHER PUBLICATIONS

JP Office Action with English summary for JP Application No. 2009-143633 mailed on Apr. 22, 2011.

(Continued)

*Primary Examiner* — Devin Henson
(74) *Attorney, Agent, or Firm* — Oliff, PLC

(57) ABSTRACT

Provided is a guidewire including a core shaft, an outer flexible tube, a stranded wire that is disposed parallel to a distal end portion of the core shaft, and an inner flexible tube that surrounds a distal end portion of the core shaft and the stranded wire. The inner flexible tube is disposed in the outer flexible tube so that a distal end thereof is positioned between the distal ends of the core shaft and the stranded wire and a proximal end of the core shaft so as to be separated from the distal ends of the core shaft and the stranded wire. A joint is formed so as to join the distal end of the inner flexible tube, the core shaft, and the stranded wire to each other.

7 Claims, 5 Drawing Sheets

(56) References Cited

FOREIGN PATENT DOCUMENTS

| | | |
|---|---|---|
| JP | 2004-190167 | 7/2004 |
| JP | 2004-313570 | 11/2004 |
| JP | B2-3586024 | 11/2004 |
| JP | 2006-511304 | 4/2006 |
| JP | 2006-511304 A | 4/2006 |
| JP | 2008-161491 | 7/2008 |
| JP | 2008-161491 A | 7/2008 |
| WO | 98/58697 A1 | 12/1998 |
| WO | 2009/039063 A1 | 3/2009 |

OTHER PUBLICATIONS

European Extended Search Report dated Oct. 1, 2010 for corresponding EP Application No. 10165923.3.

Apr. 27, 2012 Office Action issued in Chinese Patent Application No. 201010206600.5 (with translation).

Nov. 5, 2012 Office Action issued in Chinese Patent Application No. 2010102066005 (with translation).

* cited by examiner

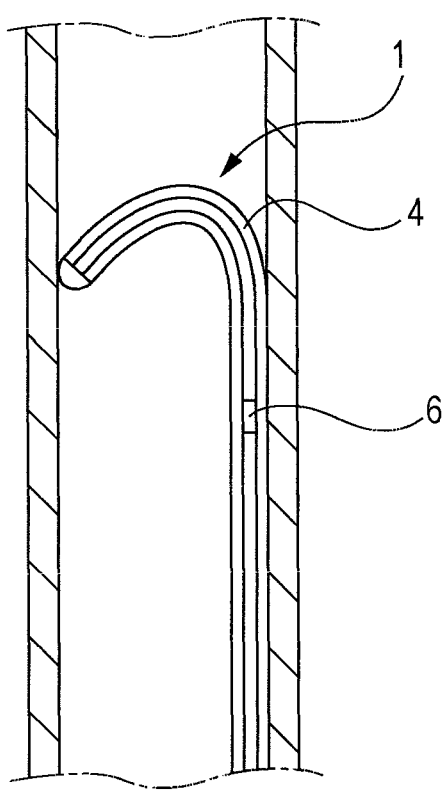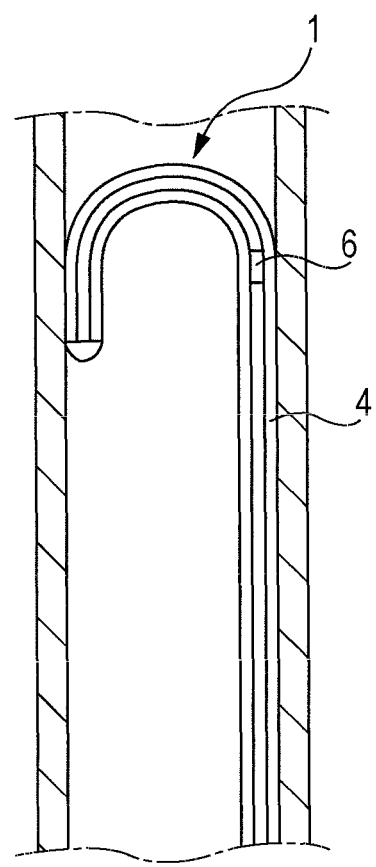

MEDICAL GUIDEWIRE

BACKGROUND OF THE INVENTION

1. Field of the Invention

The present invention relates to a medical guidewire used for medical purposes such as inserting a catheter into a blood vessel, a ureter, or an organ or inserting an indwelling device into part of a blood vessel having an aneurysm.

2. Description of the Related Art

In general, it is required that a medical guidewire have a flexible distal end portion, and it is also required that the medical guidewire smoothly transmit an operation performed at the proximal end portion to the distal end portion. In order to fulfill such requirements, a guidewire 100 of the related art includes a core shaft 101 and a coil spring 102 that surrounds the core shaft 101, and the diameter of a distal end portion 103 of the core shaft 101 is made small so as to improve flexibility (see FIG. 5).

When using the guidewire 100 to guide a device, such as a catheter or an indwelling device, to a target region in a human body, the distal end portion of the guidewire 100 may be unintentionally bent into a U-shape. For some operations, the guidewire 100 is bent into a U-shape before insertion in order to prevent misinsertion of the guidewire 100 into a nontarget blood vessel or in order that the guidewire 100 is securely held by a blood vessel wall by using the resilience of the guidewire 100.

The guidewire 100 of the related art has a low rigidity because the diameter of the distal end portion 103 of the core shaft 101 is small, so that the guidewire 100 is easily bent due to stress concentration. Once the core shaft 101 is bent into a U-shape, plastic deformation occurs, so that the core shaft 101 has a residual angle even after the U-shaped bending is released. Due to the presence of the residual angle, the operability of the guidewire 100 is reduced, and the guidewire 100 may have to be replaced during the operation.

A modification of the guidewire 100 uses a stranded wire as the distal end portion 103 of the core shaft 101 (see Japanese Unexamined Patent Application Publication No. 2008-161491). The guidewire 100 has a certain degree of resilience after having been bent. However, when the guidewire 100 is bent into a U-shape having a large curvature, the guidewire 100 may not recover its original shape even after the U-shaped bending is released. Therefore, the drawback due to the presence of a residual angle remains.

Another modification of the guidewire 100 includes a radiopaque inner coil disposed between the coil spring 102 and the core shaft 101 (see Japanese Unexamined Patent Application Publication No. 08-173547 and Japanese Unexamined Patent Application Publication (Translation of PCT Application) No. 2006-511304). With the guidewire 100, the rigidity of a part of the distal end portion having the inner coil is increased. However, this modification also has the drawback due to the presence of a residual angle after having been bent into a U-shape.

SUMMARY OF THE INVENTION

The object of the present invention, which has been achieved in order to overcome the drawback described above, is to improve the resilience of a distal end portion of a guidewire after the distal end portion has been bent into a U-shape and to prevent the U-shaped bend from becoming larger during use.

According to an aspect of the present invention, there is provided a medical guidewire (hereinafter referred to as a "guidewire") including a core shaft including a distal end portion having a small diameter; an outer flexible tube that surrounds an outer surface of the core shaft; a stranded wire disposed parallel to the distal end portion of the core shaft; and an inner flexible tube disposed in the outer flexible tube, the inner flexible tube surrounding the distal end portion of the core shaft and the stranded wire. Distal ends of the core shaft and the stranded wire are joined to a distal end of the outer flexible tube, and the inner flexible tube is disposed so that a distal end thereof is positioned between the distal ends of the core shaft and the stranded wire and a proximal end of the core shaft so as to be separated from the distal ends of the core shaft and the stranded wire.

The strands of the stranded wire can move slightly relative to each other. Therefore, the stranded wire has a high degree of freedom, a high flexibility, a high resistance to plastic deformation, and a high resilience. Therefore, by disposing the stranded wire parallel to the distal end portion of the core shaft, the resilience of the guidewire after being bent into a U-shape is improved. Moreover, the resilience of the guidewire is improved because the inner flexible tube surrounds the outer surfaces of the core shaft and the stranded wire.

The inner flexible tube is disposed so that a distal end thereof is positioned between the distal ends of the core shaft and the stranded wire and the proximal end of the core shaft so as to be separated from the distal ends of the core shaft and the stranded wire. A joint is formed so as to join the distal end of the inner flexible tube to the core shaft and the stranded wire.

With this structure, the rigidity of a portion of the guidewire between the joint and the distal end of the guidewire and the rigidity of a portion of the guidewire between the joint and the proximal end of the guidewire differ from each other. Moreover, the guidewire has a high rigidity at the joint. That is, the portion of the guidewire between the joint and the distal end is constituted by "the outer flexible tube, the core shaft, and the stranded wire" and the portion of the guidewire between the joint and the proximal end is constituted by "the outer flexible tube, the inner flexible tube, the core shaft, and the stranded wire". Therefore, these portions of the guidewire, which are divided by the joint, have different rigidities. Moreover, the guidewire has a high rigidity at the joint, because the distal end of the inner flexible tube, the core shaft, and the stranded wire are fixed to each other at the joint.

Therefore, even when the distal end portion of the guidewire is bent into a U-shape when the guidewire is inserted into the lumen of a blood vessel or the like, the portion of the guidewire between the joint and the proximal end is not bent due to the presence of the joint having a high rigidity. As a result, only the distal end portion of the guidewire, which has a high flexibility, is bent into a U-shape. That is, only the distal end portion having a high resilience is bent into a U-shape, so that the guidewire is not plastically deformed in the bent state. Therefore, the resilience of the guidewire can be improved. Even if the joint fails to stop the U-shaped bending of the guidewire and the portion of the guidewire between the joint and the proximal end is bent, the guidewire has a high resilience after the bending is released due to the presence of the inner flexible tube.

BRIEF DESCRIPTION OF THE DRAWINGS

FIGS. 3A and 3B illustrate the distal end portion of the guidewire according to the first embodiment that is being bent into a U-shape in a blood vessel;

DESCRIPTION OF THE PREFERRED EMBODIMENTS

A guidewire according to a first embodiment includes a core shaft, an outer flexible tube, a stranded wire disposed parallel to a distal end portion of the core shaft, and an inner flexible tube. The core shaft has a distal end portion having a small diameter. The outer flexible tube surrounds the outer surface of the core shaft. The inner flexible tube is disposed in the outer flexible tube and surrounds the distal end portion of the core shaft and the stranded wire. Distal ends of the core shaft and the stranded wire are joined to a distal end of the outer flexible tube. The inner flexible tube is disposed so that a distal end thereof is positioned between the distal ends of the core shaft and the stranded wire and a proximal end of the core shaft so as to be separated from the distal ends of the core shaft and the stranded wire. A joint is formed so as to join the distal end of the inner flexible tube to the core shaft and the stranded wire.

The outside diameter of the core shaft decreases stepwise toward the distal end. The inner flexible tube is a hollow stranded-wire coil made by stranding multiple metal strands. The inner flexible tube has a tapered shape in which the outside diameter gradually decreases toward the distal end. The inside diameter of the inner flexible tube is uniform from the distal end to the proximal end. The metal strands of the hollow stranded-wire coil are made of a stainless steel alloy.

The outer flexible tube is a single-wire coil including a large-pitch portion that extends from the distal end of the outer flexible tube toward the proximal end by a certain distance. The large-pitch portion has a pitch larger than that of a proximal end portion of the outer flexible tube. A proximal end of the large-pitch portion is positioned between the joint and the proximal end of the outer flexible tube.

First Embodiment

Structure of First Embodiment

Figure 1:
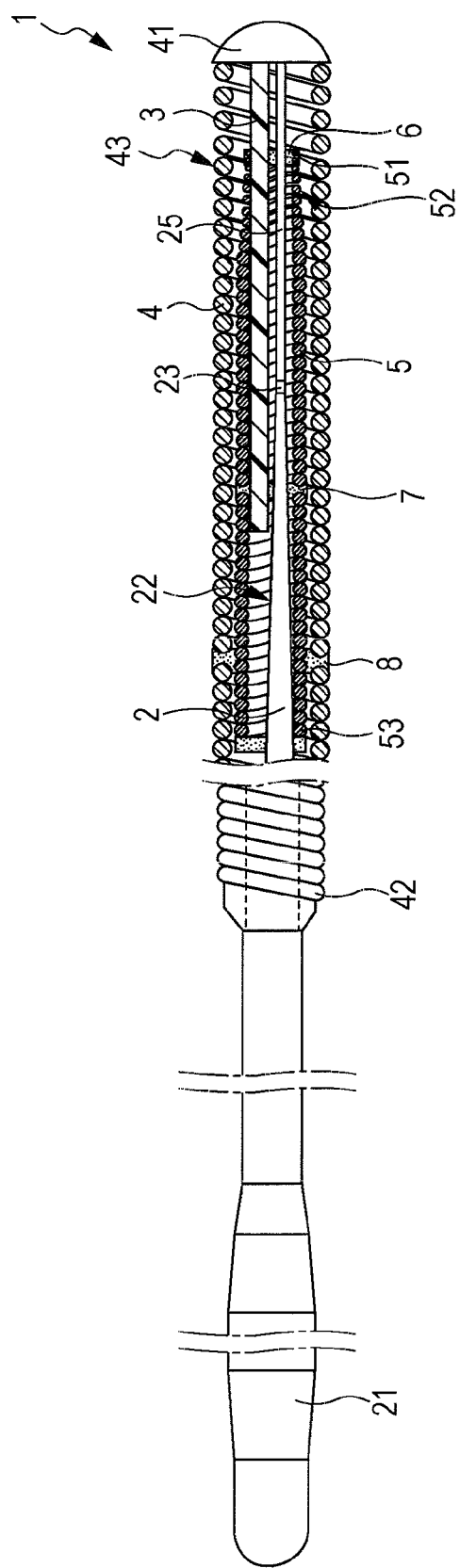
FIG. 1 is a partially sectional side view of a guidewire according to a first embodiment.
Figure 2:
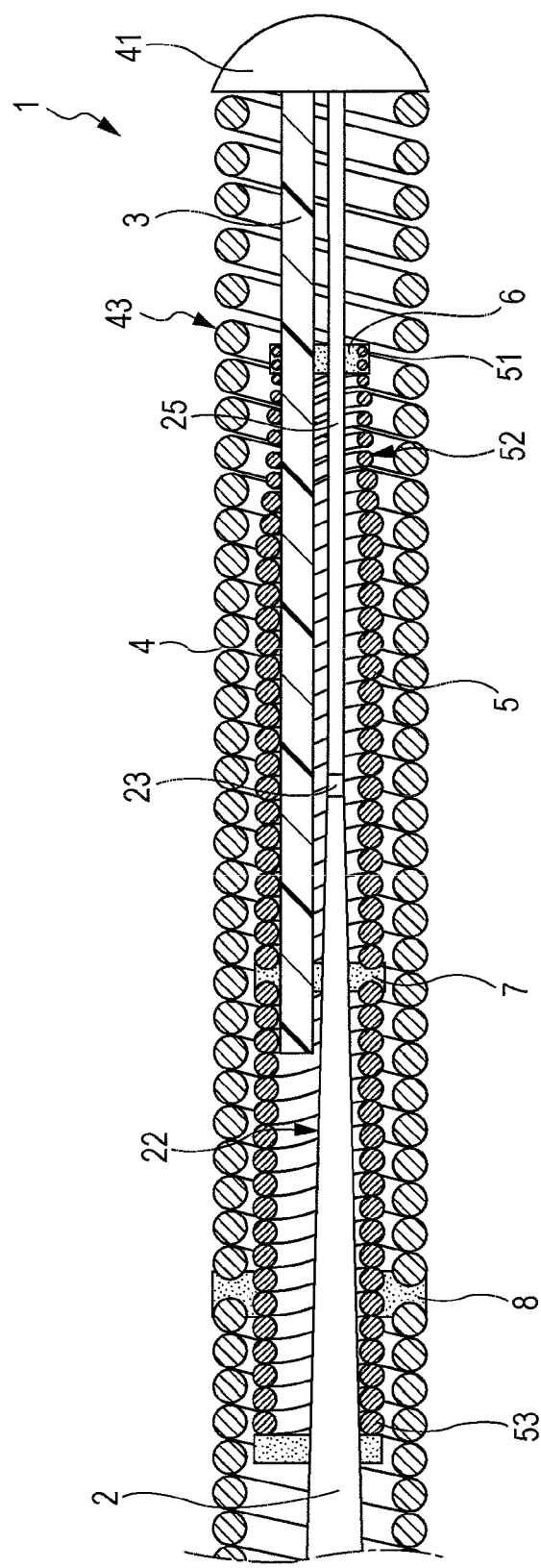
FIG. 2 is a sectional side view of a distal end portion of the guidewire according to the first embodiment.

Referring to FIGS. 1 to 3, the structure of a guidewire 1 according to the first embodiment will be described. In FIGS. 1 and 2, the right side is the distal end side, and the left side is the proximal end side. The guidewire 1 includes a core shaft 2, a stranded wire 3 disposed parallel to the core shaft 2, an outer flexible tube 4 through which the core shaft 2 and the stranded wire 3 are inserted, and an inner flexible tube 5 disposed in the outer flexible tube 4. The core shaft 2 and the stranded wire 3 are inserted through the inner flexible tube 5. The core shaft 2, the stranded wire 3, and the inner flexible tube 5 are inserted through the outer flexible tube 4.

The core shaft 2 is made of a stainless steel alloy. The core shaft 2 has a grip 21, which has a large diameter, positioned adjacent to the proximal end thereof and a distal end portion 22, which has a small diameter, positioned adjacent to the distal end thereof. The diameter of the distal end portion 22 of the core shaft 2 decreases stepwise. The distal end portion 22 of the core shaft includes a step portion 23 and a small-diameter portion 25 that extends from the step portion 23 to the distal end of the core shaft 2. In the first embodiment, the small-diameter portion 25 has an outside diameter of, for example, 0.03 mm.

The stranded wire 3 is made by stranding metal strands made of, for example, a stainless steel alloy. In the first embodiment, for example, the stranded wire 3 is made by stranding seven stainless steel strands each having an outside diameter of 0.014 mm. The stranded wire 3 is disposed parallel to the distal end portion 22 of the core shaft 2. A distal end of the stranded wire 3 and the distal end of the core shaft 2 are soldered to a brazed end portion 41 disposed at the distal end of the outer flexible tube 4. A proximal end of the stranded wire 3 is positioned between the proximal end of the small-diameter portion 25 and the proximal end of the core shaft 2. The proximal end of the stranded wire 3 and the core shaft 2 are soldered to the inner flexible tube 5 at a position between the step portion 23 and the proximal end of the core shaft 2 (a soldered portion 7).

The outer flexible tube 4 is a single-wire coil made of a stainless steel strand. In the first embodiment, for example, the stainless steel strand has an outside diameter of 0.05 mm and the outer flexible tube 4 has an outside diameter of 0.355 mm. In order to provide flexibility to the distal end portion of the outer flexible tube 4, the outer flexible tube 4 includes a large-pitch portion 43, which has a larger coil pitch, in the distal end portion thereof. The large-pitch portion 43 extends in the axial direction from the distal end of the outer flexible tube 4 to a position between a distal end 51 of the inner flexible tube 5 (described below) and the proximal end of the outer flexible tube 4. As long as the outer flexible tube 4 has flexibility, the outer flexible tube 4 need not be a single-wire coil and may instead be a hollow stranded-wire coil, a resin tube, or the like.

The outer flexible tube 4 surrounds only a distal end portion of the core shaft 2. A proximal end 42 of the outer flexible tube 4 is fixed to an outer surface of a large-diameter portion of the core shaft 2 near to the proximal end. An outer surface of the outer flexible tube 4 is coated with a hydrophilic resin.

The inner flexible tube 5 is a hollow stranded-wire coil made of multiple stainless steel strands. The hollow stranded-wire coil may be made by stranding multiple strands around a core by using a wire stranding machine and then removing the core, or by stranding multiple strands into a hollow shape. In the first embodiment, for example, the inner flexible tube 5, which has an outside diameter of 0.188 mm, is formed by stranding six stainless steel strands each having an outside diameter of 0.04 mm, so that the flexibility and the torque transmission are well balanced. A distal end portion 52 of the inner flexible tube 5 is electro-polished so that the outside diameter decreases toward the distal end. The inside diameter of the inner flexible tube 5 is uniform from the proximal end to the distal end.

The inner flexible tube 5 has an outside diameter that is smaller than the inside diameter of the outer flexible tube 4. The inner flexible tube 5 has a length in the axial direction that is smaller than that of the outer flexible tube 4. The distal end 51 of the inner flexible tube 5 is positioned between the distal end of the outer flexible tube 4 and the proximal end 42 of the outer flexible tube 4 in the axial direction. A proximal end 53 of the inner flexible tube 5 is positioned between the proximal end 42 of the outer flexible tube 4 and the distal end of the outer flexible tube 4. The inner flexible tube 5 and the outer flexible tube 4 are fixed to each other at at least one position so that relative positions thereof are fixed. In the first embodiment, the inner flexible tube 5 and the outer flexible tube 4 are fixed to each other at a position between the proximal end of the stranded wire 3 and the proximal end of the outer flexible tube 4 in the axial direction (a soldered portion 8).

The distal end 51 of the inner flexible tube 5 is positioned between the distal ends of the core shaft 2 and the stranded wire 3 and the proximal end of the small-diameter portion 25. The proximal end 53 of the inner flexible tube 5 is positioned between the proximal end of the stranded wire 3 and the proximal end of the core shaft 2. That is, the inner flexible tube 5 is disposed so that the distal end 51 of the inner flexible tube 5 is positioned between the distal ends of the core shaft 2 and the stranded wire 3 and the proximal end of the core shaft 2 so as to be separated from the distal ends of the core shaft 2 and the stranded wire 3 in the axial direction.

In the guidewire 1, a joint 6 is formed so as to join the distal end 51 of the inner flexible tube 5 to the core shaft 2 and the stranded wire 3. To be specific, the joint 6 is formed by soldering the distal end of the inner flexible tube 5, the stranded wire 3, and the core shaft 2 to each other. A proximal end of the large-pitch portion 43 is positioned between the joint 6 and the proximal end of the outer flexible tube 4. The proximal end 53 of the inner flexible tube 5 is fixed to the outer surface of the core shaft 2.

Operational Effect of First Embodiment

The guidewire 1 according to the first embodiment includes the stranded wire 3 that extends parallel to the distal end portion 22 of the core shaft 2. The diameter of the distal end portion 22 of the core shaft 2 decreases stepwise toward the distal end. The strands of the stranded wire 3 can move slightly relative to each other. Therefore, the stranded wire 3 has a high degree of freedom, a high flexibility, a high resistance to plastic deformation, and a high resilience. Therefore, by disposing the stranded wire 3, which has resistance to plastic deformation, parallel to the distal end portion 22 of the core shaft 2, which has a small diameter and thus has flexibility, the resilience of the guidewire 1 after being bent into a U-shape is improved.

The guidewire 1 further includes the inner flexible tube 5, which is disposed in the outer flexible tube 4 and surrounds the distal end portion 22 of the core shaft 2 and the stranded wire 3. With this structure, the resilience of the guidewire 1 is improved because the inner flexible tube 5 surrounds the outer surface of the core shaft 2.

The inner flexible tube 5 is disposed so that the distal end 51 thereof is positioned between the distal ends of the core shaft 2 and the stranded wire 3 and the proximal end of the core shaft 2 so as to be separated from the distal ends of the core shaft 2 and the stranded wire 3. The joint 6 is formed so as to join the distal end of the inner flexible tube 5 to the core shaft 2 and the stranded wire 3.

Thus, the rigidity of a portion of the guidewire 1 between the joint 6 and the distal end of the guidewire 1 and the rigidity of a portion of the guidewire 1 between the joint 6 and the proximal end of the guidewire 1 differ from each other. Moreover, the guidewire 1 has a high rigidity at the joint 6. That is, the portion of the guidewire 1 between the joint 6 and the distal end is constituted by "the outer flexible tube 4, the core shaft 2, and the stranded wire 3" and the portion of the guidewire 1 between the joint 6 and the proximal end is constituted by "the outer flexible tube 4, the inner flexible tube 5, the core shaft 2, and the stranded wire 3". Therefore, these portions of the guidewire 1, which are divided by the joint 6, have different rigidities. Moreover, the guidewire 1 has a high rigidity at the joint 6, because the joint 6 is formed by soldering the distal end 51 of the inner flexible tube 5, the core shaft 2, and the stranded wire 3 to each other.

Therefore, even when the guidewire 1 is bent into a U-shape when the guidewire 1 is inserted into the lumen of a blood vessel or the like, the portion of the guidewire 1 between the joint 6 and the proximal end is not bent due to the presence of the joint 6 having a high rigidity. That is, even when the guidewire 1 is unintentionally bent in a blood vessel (see FIG. 3A) and a user inserts the guidewire 1 deeper into the blood vessel, the bending stops in front of the joint 6 because the joint 6 has a high rigidity (see FIG. 3B). Therefore, the U-shaped bend does not become larger. During an operation in which a user intentionally bends the guidewire 1 into a U-shape and then inserts the guidewire 1, a portion of the guidewire 1 between the joint 6 and the proximal end is not easily bent.

As a result, only the distal end portion of the guidewire 1, which has a high flexibility, is bent into a U-shape. That is, only the distal end portion having a high resilience is bent into a U-shape, so that the guidewire 1 is not plastically deformed in the bent state. Therefore, the resilience of the guidewire 1 is improved. Even if the joint 6 fails to stop the U-shaped bending of the guidewire 1 and the portion of the guidewire between the joint 6 and the proximal end is bent, the guidewire 1 has a high resilience after the bending is released due to the presence of the inner flexible tube 5.

The outer flexible tube 4 is a single-wire coil including the large-pitch portion 43 that extends from the distal end of the outer flexible tube 4 toward the proximal end by a certain distance. The large-pitch portion 43 has a pitch larger than that of a proximal end portion of the outer flexible tube 4. A proximal end of the large-pitch portion 43 is positioned between the joint 6 and the distal end of the outer flexible tube 4. With this structure, the distal end of the guidewire 1 has flexibility, and the guidewire 1 has a smoother gradation in rigidity.

That is, the guidewire 1 according to the first embodiment has a structure having a gradation in rigidity in which the flexural rigidity gradually increases from the distal end toward the proximal end. To be specific, in the guidewire 1, a portion constituted by "the large-pitch portion 43 of the outer flexible tube 4, the core shaft 2, and the stranded wire 3", a portion constituted by "the large-pitch portion 43 of the outer flexible tube 4, the inner flexible tube 5, the core shaft 2, and the stranded wire 3", and a portion constituted by "a normal-pitch portion of the outer flexible tube 4, the inner flexible tube 5, the core shaft 2, and the stranded wire 3" are arranged in this order from the distal end of the guidewire 1. The flexural rigidity gradually increases in this order. The remaining portion of the guidewire 1 near to the proximal end has a higher flexural rigidity, because the core shaft 2 tapers. Therefore, occurrence of stress concentration due to a sharp difference in rigidity is suppressed, so that the torque transmission is improved.

Because a hollow stranded-wire coil is used as the inner flexible tube 5, the torque transmission is improved as compared with a case in which a single-wire coil is used as the inner flexible tube 5. Therefore, a user can operate the guidewire 1 at will, so that the treatment time can be reduced. The distal end portion 52 of the inner flexible tube 5 has a tapered shape in which the diameter gradually decreases toward the distal end. Therefore, the gradation in the rigidity of the guidewire 1 can be made more moderate and smoother. The distal end portion of the inner flexible tube 5 has a small diameter, so that the flexibility of the guidewire 1 is improved and the guidewire 1 can be more easily inserted into a peripheral lumen.

The inside diameter of the inner flexible tube 5 is uniform from the distal end to the proximal end. Therefore, the core shaft 2 and the stranded wire 3 can be easily inserted into the inner flexible tube 5, so that the guidewire 1 can be easily assembled.

The metal strands of the hollow stranded-wire coil are made of a stainless steel alloy. Therefore, the rigidity of the inner flexible tube 5 is increased, so that the torque transmission and the operability of the guidewire 1 are improved.

Modification

In the first embodiment, the diameter of the distal end portion 22 of the core shaft 2 decreases stepwise toward the distal end. Alternatively, the distal end portion 22 may be tapered toward the distal end.

In the first embodiment, the core shaft 2 is made of a stainless steel alloy. Alternatively, a part of the core shaft 2 near to the distal end (at least the small-diameter portion 25) may be made of a pseudoelastic alloy having a high resilience (for example, Ni—Ti alloy), and a part of the core shaft 2 near to the proximal end may be made of a stainless steel alloy. With this structure, the resilience of the distal end portion of the guidewire 1 is improved, and the torque transmission and the operability of the guidewire 1 are improved.

Figure 4:
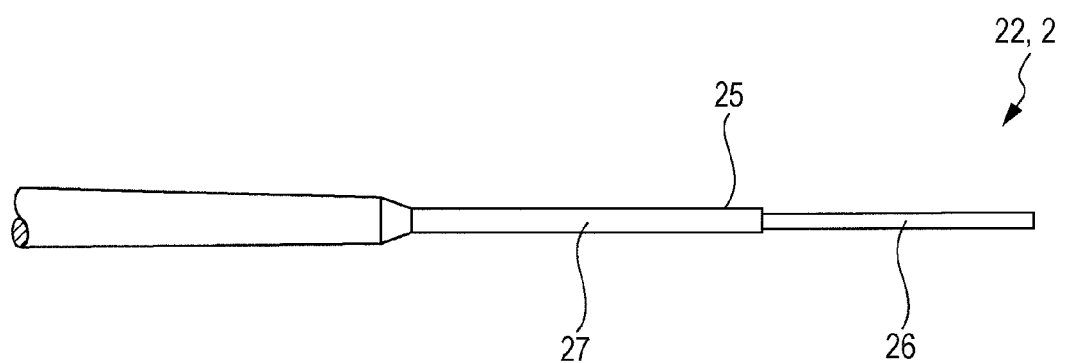
FIG. 4 is a partial side view of a core shaft of a guidewire according to a modification.
Figure 5:
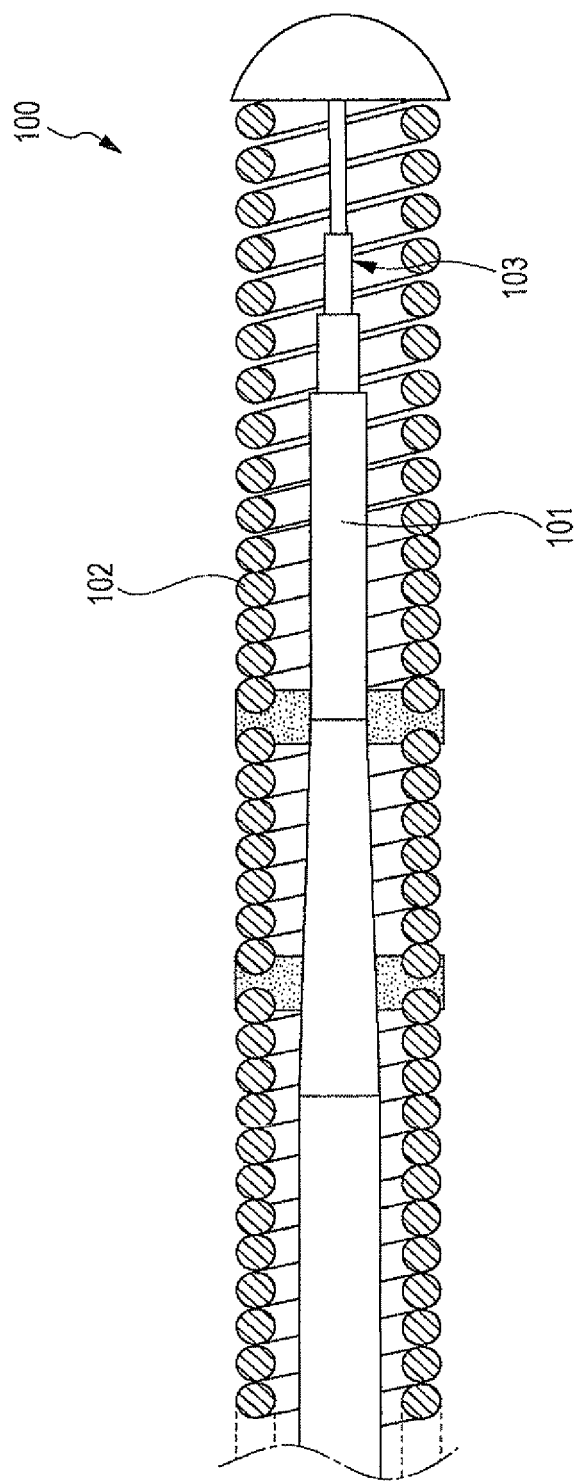
FIG. 5 is a sectional side view of a distal end portion of a guidewire of the related art.

As illustrated in FIG. 4, a part of the small-diameter portion 25 near to the distal end may be made of a stainless steel alloy (a first distal end portion 26), a part of the small-diameter portion 25 near to the proximal end may be made of a pseudoelastic alloy (a second distal end portion 27), and a part of the core shaft 2 between the small-diameter portion 25 and the proximal end of the core shaft 2 may be made of a stainless steel alloy. With this structure, the pseudoelastic alloy improves the resilience of the distal end portion 22 of the core shaft 2. Moreover, because the portions made of a stainless steel alloy are provided to both sides of the part made of a pseudoelastic alloy, a torque applied to the proximal end portion of the guidewire 1 can be reliably transmitted to the distal end portion, so that the torque transmission and the operability of the guidewire 1 can be further improved.

In the first embodiment, the distal end portion 52 of the inner flexible tube 5 is tapered toward the distal end. Alternatively, the diameter of the distal end portion 52 may decrease stepwise toward the distal end.

In the first embodiment, the inner flexible tube 5 is made of only stainless steel strands. Alternatively, the inner flexible tube 5 may be made of only pseudoelastic alloy strands. With this structure, the resilience of the inner flexible tube 5 can be further increased. As a further alternative, the inner flexible tube 5 may be formed by combining stainless steel strands and pseudoelastic alloy strands (for example, three stainless steel strands and three pseudoelastic alloy strands). In this case, the stainless steel alloy increases the rigidity of the inner flexible tube 5, while the pseudoelastic alloy increases the resilience of the inner flexible tube 5. Therefore, the torque transmission, the operability, and the resilience of the guidewire 1 can be improved.

In the first embodiment, the outer flexible tube 4 surrounds only the distal end portion of the core shaft 2. Alternatively, the outer flexible tube 4 may surround the entirety of the core shaft 2.

The present invention contains subject matter related to Japanese Patent Application No. 2009-143633 filed in the Japan Patent Office on Jun. 16, 2009, the entire contents of which are incorporated herein by reference.

What is claimed is:

1. A medical guidewire comprising:
   a core shaft including a distal end portion having a small diameter;
   an outer coil that surrounds an outer surface of the core shaft;
   a stranded wire disposed parallel to the distal end portion of the core shaft;
   a brazed end portion joining the distal end portion of the core shaft, a distal portion of the stranded wire and a distal end portion of the outer coil;
   an inner flexible tube disposed entirely within the outer coil, the inner flexible tube surrounding the distal end portion of the core shaft and the stranded wire, wherein the inner flexible tube is disposed so that a distal end thereof is positioned between the brazed end portion and a proximal end of the core shaft so as to be separated from the brazed end portion, and
   a joint is formed so as to join the distal end of the inner flexible tube to the core shaft and the stranded wire without jointing to the outer coil.

2. The medical guidewire according to claim 1, wherein the inner flexible tube has a tapered shape in which an outside diameter gradually decreases toward the distal end thereof so that a gap between the inner flexible tube and the outer coil increases toward the distal end of thereof.

3. The medical guidewire according to claim 2, wherein an inside diameter of the inner flexible tube is uniform from the distal end to a proximal end thereof.

4. The medical guidewire according to claim 1, wherein an outside diameter of the inner flexible tube decreases stepwise toward the distal end thereof so that a gap between the inner flexible tube and the outer coil increases toward the distal, end of thereof.

5. The medical guidewire according to claim 4, wherein an inside diameter of the inner flexible tube is uniform from the distal end to a proximal end thereof.

6. The medical guidewire according to claim 1, wherein the inner flexible tube is a hollow stranded-wire coil in which a plurality of metal strands are stranded.

7. The medical guidewire according to claim 1, wherein the outer coil is a single-wire coil including a large-pitch portion extending from the distal end of the outer coil toward the proximal end of the outer coil by a predetermined distance, the large-pitch portion having a pitch that is larger than a pitch of a proximal end portion of the outer coil, and
   a proximal end of the large-pitch portion is positioned between the joint and the proximal end of the outer coil.

* * * * *